(12) United States Patent
Noro et al.

(10) Patent No.: US 11,342,077 B2
(45) Date of Patent: May 24, 2022

(54) MEDICAL INFORMATION PROCESSING APPARATUS AND MEDICAL INFORMATION PROCESSING METHOD

(71) Applicant: CANON MEDICAL SYSTEMS CORPORATION, Otawara (JP)

(72) Inventors: Kazumasa Noro, Shioyagun (JP); Yusuke Kano, Nasushiobara (JP); Kazuki Utsunomiya, Nasushiobara (JP); Longxun Piao, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 125 days.

(21) Appl. No.: 16/218,676

(22) Filed: Dec. 13, 2018

(65) Prior Publication Data

US 2019/0189282 A1    Jun. 20, 2019

(30) Foreign Application Priority Data

Dec. 14, 2017   (JP) .............................. JP2017-239849

(51) Int. Cl.
*G16H 50/30*   (2018.01)
*A61B 5/00*   (2006.01)
*G16H 50/20*   (2018.01)

(52) U.S. Cl.
CPC ........... *G16H 50/30* (2018.01); *A61B 5/7275* (2013.01); *G16H 50/20* (2018.01)

(58) Field of Classification Search
CPC ........ G16H 10/60; G16H 15/00; G16H 40/20; G16H 40/40; G16H 50/30; A61B 5/7275
See application file for complete search history.

(56) References Cited

U.S. PATENT DOCUMENTS

| 5,942,986 A * | 8/1999 | Shabot | G16H 40/67 340/7.29 |
| 2003/0023178 A1* | 1/2003 | Bischoff | A61B 5/364 600/515 |
| 2007/0257788 A1* | 11/2007 | Carlson | G08B 25/04 340/506 |

(Continued)

FOREIGN PATENT DOCUMENTS

| JP | 2012-247879 | 12/2012 |
| JP | 2016-21189 | 2/2016 |
| WO | WO 2008/013193 A1 | 1/2008 |

*Primary Examiner* — John P Go
(74) *Attorney, Agent, or Firm* — Oblon, McClelland, Maier & Neustadt, L.L.P.

(57) ABSTRACT

A medical information processing apparatus according to an embodiment includes: a display controlling unit configured to display, in a time series, events of diagnosis and treatment actions performed on a subject during a designated display period; a tallying unit configured to tally, as an index value, numerical values either extracted or calculated on the basis of information about the events, for each of tally units obtained by dividing the display period into sections arranged in a time series; and a calculating unit configured to calculate a piece of context information relatively indicating one selected from between the diagnosis and treatment actions and a state of the subject in each of the tally units, by comparing the index values tallied for the tally units with one another, and to further display the pieces of context information so as to be kept in association with the events.

13 Claims, 27 Drawing Sheets

(56) References Cited

U.S. PATENT DOCUMENTS

| | | | |
|---|---|---|---|
| 2009/0024411 A1* | 1/2009 | Albro | G16H 15/00 |
| | | | 705/2 |
| 2009/0082640 A1* | 3/2009 | Kovach | A61B 5/743 |
| | | | 600/300 |
| 2009/0254370 A1 | 10/2009 | Kondo et al. | |
| 2011/0046975 A1* | 2/2011 | Hoffman | G06F 16/24573 |
| | | | 705/2 |
| 2011/0227739 A1* | 9/2011 | Gilham | G16H 40/63 |
| | | | 340/573.1 |
| 2012/0320716 A1* | 12/2012 | DiMaggio | G06Q 10/109 |
| | | | 368/29 |
| 2013/0027411 A1* | 1/2013 | Hebler | G16H 40/67 |
| | | | 345/501 |
| 2013/0111387 A1 | 5/2013 | Li et al. | |
| 2013/0209068 A1* | 8/2013 | Lynn | G16H 40/60 |
| | | | 386/278 |

* cited by examiner

FIG.3

| | 2017/4/11 10:00 TO 2017/4/18 10:00 | 2017/4/18 10:00 TO 2017/4/25 10:00 | 2017/4/25 10:00 TO 2017/5/2 10:00 | ⋮ | 2017/7/4 10:00 TO 2017/7/11 10:00 |
|---|---|---|---|---|---|
| VITAL SIGNS | 〰 | | | ⋮ | 〰 |
| SPECIMEN TESTS | | 🔔 | | ⋮ | |
| IMAGING TESTS | | 🅰 | 🅰 | ⋮ | |
| PRESCRIPTIONS | 💊 | | 💊 | ⋮ | |
| NURSING RECORDS | 👤 | | 👤 | ⋮ | 👤 |

18:32 Imaging (Echo)
18:33 Imaging (Echo)
18:52 Imaging (CT)

FIG.4

| DISPLAY PERIOD | TALLY UNIT |
|---|---|
| 3 OR MORE YEARS | 1 YEAR |
| 6 MONTHS - 3 YEARS | 1 MONTH |
| 2 MONTHS - 6 MONTHS | 1 WEEK |
| 2 WEEKS - 2 MONTHS | 3 DAYS |
| 5 DAYS - 2 WEEKS | 1 DAY |
| 1 DAY - 5 DAYS | 6 HOURS |
| ⋮ | ⋮ |

FIG.5

| 2017/4/11 10:00 TO 2017/4/18 10:00 | 2017/4/18 10:00 TO 2017/4/25 10:00 | 2017/4/25 10:00 TO 2017/5/2 10:00 | ... | 2017/7/4 10:00 TO 2017/7/11 10:00 |

FIG.6

| PATIENT ID | TYPE OF VITAL SIGN | MEASURED DATE/TIME | MEASURED VALUE |
|---|---|---|---|
| P0001 | PULSE RATE | 20170611 09:15 | 65 |
| P0001 | BLOOD PRESSURE | 20170611 09:15 | 139/91 |
| P0001 | BODY TEMPERATURE | 20170611 09:15 | 36.4 |
| ... | ... | ... | ... |

FIG.7

| TYPE OF VITAL SIGN | REFERENCE RANGE |
|---|---|
| PULSE RATE | 60-100 |
| BLOOD PRESSURE | LOWER THAN 130/85 |
| BODY TEMPERATURE | 36-37 |
| ... | ... |

FIG.8

| VITAL SIGNS | 2017/4/11 10:00 TO 2017/4/18 10:00 | 2017/4/18 10:00 TO 2017/4/25 10:00 | 2017/4/25 10:00 TO 2017/5/2 10:00 | ... | 2017/7/4 10:00 TO 2017/7/11 10:00 |
|---|---|---|---|---|---|
| | 3 | 10 | 25 | ... | 8 |

FIG.9

| PATIENT ID | DATE/TIME | DATA |
|---|---|---|
| P0001 | 20170611 09:15 | 201706110915_P0001.dcm |
| P0001 | 20170612 11:30 | 201706121130_P0001.dcm |
| P0001 | 20170613 14:00 | 201706131400_P0001.dcm |
| ... | ... | ... |

FIG.10

| IMAGING TESTS | 2017/4/11 10:00 TO 2017/4/18 10:00 | 2017/4/18 10:00 TO 2017/4/25 10:00 | 2017/4/25 10:00 TO 2017/5/2 10:00 | ... | 2017/7/4 10:00 TO 2017/7/11 10:00 |
|---|---|---|---|---|---|
| | 1 | 2 | 4 | ... | 1 |

FIG.11

| UID | UID name |
|---|---|
| 1.2.840.10008.5.1.4.1.1.1 | Computed Radiography Image Storage |
| 1.2.840.10008.5.1.4.1.1.1.1 | Digital X-Ray Image Storage - For Presentation |
| 1.2.840.10008.5.1.4.1.1.1.1.1 | Digital X-Ray Image Storage - For Processing |
| 1.2.840.10008.5.1.4.1.1.1.2 | Digital Mammo Image Storage - For Presentation |
| 1.2.840.10008.5.1.4.1.1.1.2.1 | Digital Mammo Image Storage - For Processing |
| 1.2.840.10008.5.1.4.1.1.1.3 | Digital Intra-Oral Image Storage - For Presentation |
| 1.2.840.10008.5.1.4.1.1.1.3.1 | Digital Intra-Oral Image Storage - For Processing |
| 1.2.840.10008.5.1.4.1.1.12.1 | X-Ray Angiographic Image Storage |
| 1.2.840.10008.5.1.4.1.1.12.1.1 | Enhanced XA Image Storage |
| 1.2.840.10008.5.1.4.1.1.12.2 | X-Ray Radiofluoroscopic Image Storage |
| 1.2.840.10008.5.1.4.1.1.12.2.1 | Enhanced XRF Image Storage |
| 1.2.840.10008.5.1.4.1.1.13.1.1 | X-Ray 3D Angiographic Image Storage |
| 1.2.840.10008.5.1.4.1.1.13.1.2 | X-Ray 3D Craniofacial Image Storage |
| 1.2.840.10008.5.1.4.1.1.7 | Secondary Capture Image Storage |

FIG.12

| PATIENT ID | DATE/TIME | DATA |
|---|---|---|
| P0001 | 2017/05/10 09:00 | DRUG A |
| P0001 | 2017/05/10 13:00 | DRUG B |
| P0001 | 2017/05/10 17:00 | DRUG A |
| P0001 | 2017/05/11 09:00 | DRUG C |
| P0001 | 2017/05/11 13:00 | DRUG D |
| ... | ... | ... |

FIG.13

| | 2017/4/11 10:00 TO 2017/4/18 10:00 | 2017/4/18 10:00 TO 2017/4/25 10:00 | 2017/4/25 10:00 TO 2017/5/2 10:00 | ... | 2017/7/4 10:00 TO 2017/7/11 10:00 |
|---|---|---|---|---|---|
| PRESCRIPTIONS | 1 | 3 | 5 | ... | 2 |

FIG.14

| PATIENT ID | DATE/TIME | DATA |
|---|---|---|
| P0001 | 20170611 09:15 | Xxx |
| P0001 | 20170612 11:30 | Yyy |
| P0001 | 20170613 14:00 | Zzz |
| P0001 | ... | ... |

FIG.15

STEP 0: PREPARATION - RECORDED AT 8:15
S) FEVER AND COUGH FOR LAST 4 DAYS. CANNOT MOVE / NO RESPONSE
O) JCS100, BP80/46, HR128/REG. PULSE, RR28, $SpO_2$ 96% (4L), BT37.8
   4 L WITH OXYGEN MASK, NO TUBES, LAST MEAL TAKEN 1 DAY AGO. (1)
A) ACUTE FEVER AND SHOCK WITH RESPIRATORY FAILURE: POSSIBILITY OF
   SEPTICEMIA. (2)
P) Tx) OXYGEN, MASK WITH RESERVOIR, 2 TUBES FOR NORMAL SALINE. (3)
   Dx) ABCDE + ABDOMEN ECHO (FOCUS ON HEPATOBILIARY) + GRAM STAINING (SPUTUM/
   URINE, BLOOD CULTURE 2 SETS) (4)

STEP 1: URGENCY EVALUATION AND STABILIZATION - RECORDED AT 8:35
S) PATIENT CANNOT ANSWER Q'S; FAMILY REPORTED COUGH AND SHORT OF BREATH.
O) GENERAL APPEARANCE: CONDITION SERIOUS, LOOKS SLUGGISH.
   FIRST IMPRESSION: BREATHING FAST, FAST PULSE, COLD SWEAT, NO RESPONSE.
   VITAL SIGNS:  JCS200, BP76/44, HR132/REG. PULSE, RR30, $SpO_2$ 96% (6L), BT37.4
   JUGULAR COLLAPSE, LEG EDEMA (±), PERIPHERY COLD SWEAT (-), PERSPIRATION (+),
   PULMONARY RALES (+), ABDOMINAL PRESSURE PAIN? (5)
A) MOST LIKELY PNEUMONIA SEPTICEMIA; ALSO CHECK FOR ANAPHYLAXIS AND ADRENAL
   INSUFFICIENCY. (6)
P) Tx) NORMAL SALINE IV - 1 L AT A TIME TO SEE REACTION.
   Dx) TESTS AS PLANNED, URGENT CXR AND SPUTUM TESTS IN PARTICULAR, ADD CARDIAC
   ECHO TO MAKE SURE. (7)

STEP 2: CONFIRMED DIAGNOSIS AND SPECIFIC TREATMENT - RECORDED AT 9:03
S) COUGH FOR LAST 4 DAYS, DID NOT GET UP IN THE MORNING, DID NOT RESPOND TO
   FAMILY AROUND MIDDAY, CALLED AMBULANCE. (SYMPTOMS AND MEDICAL HISTORY ARE
   OMITTED TO SAVE SPACE)
O) DETAILED OBSERVATIONS (OMITTED); CXR: INFILTRATIVE SHADOW IN LOWER RIGHT LUNG
   FIELD,
   SPUTUM GRAM STAINING: LANCET SHAPED GPC;
   1.5 L NORMAL SALINE MADE IMPROVEMENT TO BP 110/76, HR 98.
   $SpO_2$ 92%, RR 30 WITH 8 L $O_2$. JCS 20.
A) DIAGNOSED AS SERIOUS SEPTICEMIA CAUSED BY PNEUMONIA FROM STREPTOCOCCUS
   PNEUMONIAE.
   WORSENING TYPE 1 RESPIRATORY INSUFFICIENCY AND ACUTE NEPHROPATHY, IMPAIRED
   CONSCIOUSNESS, AND ANEMIA. RECOVERED FROM SHOCK. (8)
P) Tx) START TREATMENT WITH 2g OF AMPICILLIN. $O_2$ CHANGED TO 10 L.
   Ex) BECAUSE PATIENT CANNOT TALK, PLAN WAS DISCUSSED WITH FAMILY.

STEP 3: DECIDE DEFINITIVE PLAN - RECORDED AT 9:21
S) PATIENT'S ADVANCED DIRECTIVE IS UNKNOWN. FAMILY WANTS MAXIMUM TREATMENT.
   PULMONOLOGIST ALSO AGREED WITH PNEUMONIA DIAGNOSIS. EMERGENCY
   CONSULTING DOCTOR WAS CONSULTED TO DECIDE TO START TREATMENT AT ICU.
O) PATIENT'S SON AND SON'S WIFE HAD A MEETING WITH CONSULTING DOCTOR TO
   UNDERSTAND SITUATION.
   (SEE SEPARATE SHEET FOR MEETING DETAILS) (9)
A) SERIOUS SEPTICEMIA CAUSED BY PNEUMONIA FROM STREPTOCOCCUS PNEUMONIAE.
   WILL NEED MONITORING WITH ARTIFICIAL RESPIRATOR.
P) ACCEPTED AT ICU. SYMPTOMS AND TREATMENT PLANS HANDED OVER TO ICU DOCTORS.

FIG.16

| | 2017/4/11 10:00 TO 2017/4/18 10:00 | 2017/4/18 10:00 TO 2017/4/25 10:00 | 2017/4/25 10:00 TO 2017/5/2 10:00 | ... | 2017/7/4 10:00 TO 2017/7/11 10:00 |
|---|---|---|---|---|---|
| NURSING RECORDS | 2 | 4 | 6 | ... | 2 |

FIG.17

| NURSING RECORDS | 2017/4/11 10:00 TO 2017/4/18 10:00 | 2017/4/18 10:00 TO 2017/4/25 10:00 | 2017/4/25 10:00 TO 2017/5/2 10:00 | ... | 2017/7/4 10:00 TO 2017/7/11 10:00 |
|---|---|---|---|---|---|
| | 1246 | 3576 | 2301 | ... | 1850 |

FIG.19

| NORMALIZED VALUE | COLOR | COLOR CODE |
|---|---|---|
| 0 TO 0.33 | BLUE | #0000ff |
| 0.33 TO 0.66 | YELLOW | #ffff00 |
| 0.66 TO 1 | RED | #ff0000 |

FIG.26

| LIST OF CRITICAL DRUGS |
|---|
| DRUG A |
| DRUG C |
| DRUG E |
| ⋮ |

FIG.27

| PATIENT ID | DATE/TIME | SPECIFICS OF EVENT |
|---|---|---|
| P0001 | 20170611 09:15 | HOSPITALIZATION |
| P0001 | 20170612 11:30 | SUDDEN CHANGE IN PATIENT'S CONDITION |
| P0001 | 20170613 14:00 | STABILIZATION OF PATIENT'S CONDITION |
| P0001 | ... | ... |

FIG.28

| EVENTS (SUDDEN CHANGE IN PATIENT'S CONDITION + STABILIZATION OF PATIENT'S CONDITION) | 2017/4/11 10:00 TO 2017/4/18 10:00 | 2017/4/18 10:00 TO 2017/4/25 10:00 | 2017/4/25 10:00 TO 2017/5/2 10:00 | ... | 2017/7/4 10:00 TO 2017/7/11 10:00 |
|---|---|---|---|---|---|
| | 2 | 5 | 1 | ... | 0 |

MEDICAL INFORMATION PROCESSING APPARATUS AND MEDICAL INFORMATION PROCESSING METHOD

CROSS-REFERENCE TO RELATED APPLICATIONS

This application is based upon and claims the benefit of priority from Japanese Patent Application No. 2017-239849, filed on Dec. 14, 2017, the entire contents of which are incorporated herein by reference.

FIELD

Embodiments described herein relate generally to a medical information processing apparatus and a medical information processing method.

BACKGROUND

Conventionally, diagnosis and treatment data used at medical sites includes various types of data such as image data, medical record data, and the like. Medical doctors perform diagnosis and treatment processes on examined subjects (e.g., patients) by viewing information from the various types of data in a comprehensive manner. For this reason, at medical sites, there is a demand for a system capable of displaying various types of diagnosis and treatment data in a time series on a single screen, the various types of data being necessary when medical doctors explore diagnoses and treatment plans or assess effects of treatments. In particular, there is a demand for the capability to view, in a bird's-eye perspective, occurrence times of various types of data related to drug administration, medical tests, vital sign measured values, and the like, as well as events of diagnosis and treatment actions performed during certain time periods.

BRIEF DESCRIPTION OF THE DRAWINGS

FIG. 3 is a drawing illustrating an example of information displayed in a timeline display region by the display controlling function according to the present embodiment;

FIG. 4 is a drawing illustrating an example of a display period/tally unit conversion table referred to by a tallying function according to the present embodiment;

FIG. 5 is a drawing illustrating an example of a display period dividing process performed by the tallying function according to the present embodiment;

FIG. 6 is a drawing illustrating an example of vital sign data referred to by the tallying function according to the present embodiment;

FIG. 7 is a drawing illustrating an example of a reference range table referred to by the tallying function according to the present embodiment;

FIG. 8 is a drawing illustrating an example of a tallying process related to vital signs and performed by the tallying function according to the present embodiment;

FIG. 9 is a drawing illustrating an example of image data referred to by the tallying function according to the present embodiment;

FIG. 10 is a drawing illustrating an example of a tallying process related to imaging tests and performed by the tallying function according to the present embodiment;

FIG. 11 is a drawing illustrating examples of a Digital Imaging and Communications in Medicine (DICOM) tag (0008,0016) referred to by the tallying function according to the present embodiment;

FIG. 12 is a drawing illustrating an example of prescription data referred to by the tallying function according to the present embodiment;

FIG. 13 is a drawing illustrating an example of a tallying process related to prescriptions and performed by the tallying function according to the present embodiment;

FIG. 14 is a drawing illustrating an example of nursing record data referred to by the tallying function according to the present embodiment;

FIG. 15 is a drawing illustrating another example of the nursing record data referred to by the tallying function according to the present embodiment;

FIG. 16 is a drawing illustrating an example of a tallying process related to nursing records and performed by the tallying function according to the present embodiment;

FIG. 17 is a drawing illustrating another example of the tallying process related to the nursing records and performed by the tallying function according to the present embodiment;

FIG. 19 is a drawing illustrating another example of the context information calculating and displaying processes performed by the calculating function according to the present embodiment;

FIG. 26 is a drawing illustrating an example of a critical drug list table referred to by a tallying function according to a modification example of the present embodiment;

FIG. 27 is a drawing illustrating an example of critical event data referred to by a tallying function according to another modification example of the present embodiment;

FIG. 28 is a drawing illustrating an example of a tallying process related to critical events and performed by a tallying function according to yet another modification example of the present embodiment;

DETAILED DESCRIPTION

A medical information processing apparatus according to an embodiment includes a display controlling unit, a tallying unit, and a calculating unit. The display controlling unit is configured to display, in a time series, events of diagnosis and treatment actions performed on a subject during a designated display period. The tallying unit is configured to tally, as an index value, numerical values either extracted or calculated on the basis of information about the events, for each of tally units obtained by dividing the display period into sections arranged in a time series. The calculating unit is configured to calculate a piece of context information relatively indicating one selected from between the diagnosis and treatment actions and a state of the subject in each of the tally units, by comparing the index values tallied for the tally units with one another, and to further display the pieces of context information so as to be kept in association with the events.

Exemplary embodiments of a medical information processing apparatus and a medical information processing method will be explained below in detail, with reference to the accompanying drawings.

Figure 1:
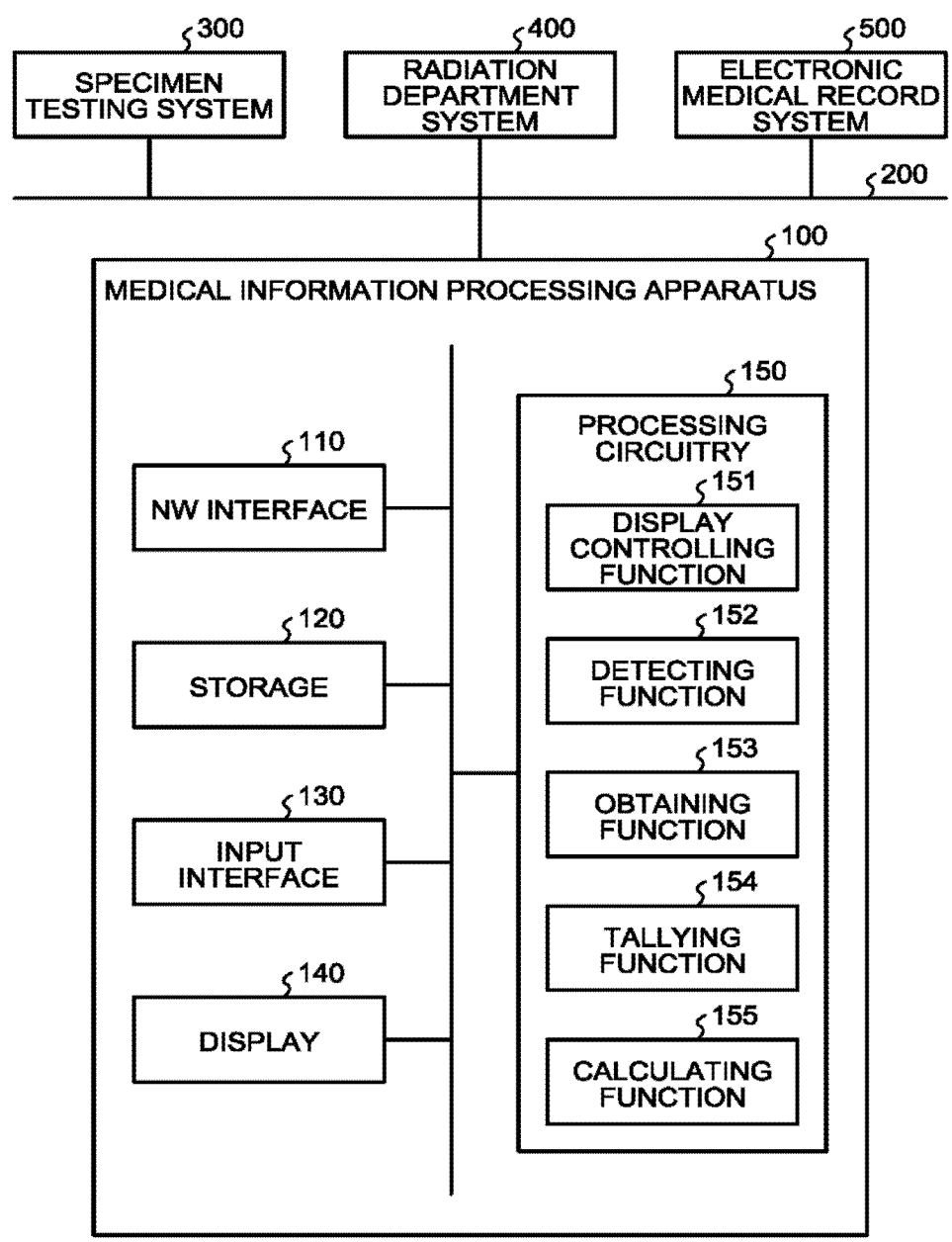
FIG. 1 is a diagram illustrating an exemplary configuration of a medical information processing apparatus according to an embodiment.

FIG. 1 is a diagram illustrating an exemplary configuration of a medical information processing apparatus according to an embodiment of the present disclosure. For example, as illustrated in FIG. 1, a medical information processing apparatus 100 according to the present embodiment is connected to a specimen testing system 300, a radiation department system 400, an electronic medical record system 500, and the like via a network 200 so as to be able to communicate with each of the systems. For example, the medical information processing apparatus 100 and the systems are installed in a hospital or the like and are connected to one another via the network 200 realized with an intra-hospital Local Area Network (LAN) or the like.

The specimen testing system 300 is configured to generate diagnosis and treatment data related to a specimen test performed on a subject and to store the generated data into a storage provided in the system. Further, in response to a request from the medical information processing apparatus 100, the specimen testing system 300 is configured to transmit the diagnosis and treatment data stored in the storage, to the medical information processing apparatus 100.

The radiation department system 400 is configured to generate diagnosis and treatment data related to a vital sign test or an imaging test performed on the subject and to store the generated data into a storage provided in the system. For example, the radiation department system 400 may include a Picture Archiving and Communication System (PACS) or the like. Further, examples of the imaging test include a medical examination using a Computed Tomography (CT) image taken by using an X-ray CT apparatus, a medical examination using a Magnetic Resonance (MR) image taken by using a Magnetic Resonance Imaging (MRI) apparatus, a medical examination using an ultrasound image taken by using an ultrasound diagnosis apparatus, and a medical examination using an X-ray image taken by an X-ray diagnosis apparatus. Further, in response to a request from the medical information processing apparatus 100, the radiation department system 400 is configured to transmit the diagnosis and treatment data stored in the storage, to the medical information processing apparatus 100.

The electronic medical record system 500 is configured to generate diagnosis and treatment data related to a prescription or a nursing record prepared for the subject and to store the generated data into a storage provided in the system. Further, in response to a request from the medical information processing apparatus 100, the electronic medical record system 500 is configured to transmit the diagnosis and treatment data stored in the storage, to the medical information processing apparatus 100.

The medical information processing apparatus 100 is configured to obtain, via the network 200, any of the various types of diagnosis and treatment data from the specimen testing system 300, the radiation department system 400, and the electronic medical record system 500 and to perform various types of information processing processes by using the obtained diagnosis and treatment data. For example, the medical information processing apparatus 100 is realized by using a computer device such as a workstation, a personal computer, a tablet terminal device, or the like.

More specifically, the medical information processing apparatus 100 includes a network (NW) interface 110, a storage 120, an input interface 130, a display 140, and processing circuitry 150.

The NW interface 110 is connected to the processing circuitry 150 and is configured to control various types of data transfers and communication performed between the medical information processing apparatus 100 and the systems. More specifically, the NW interface 110 is configured to receive the diagnosis and treatment data from the systems and to output the received diagnosis and treatment data to the processing circuitry 150. For example, the NW interface 110 is realized by using a network card, a network adapter, a Network Interface Controller (NIC), or the like.

The storage 120 is connected to the processing circuitry 150 and is configured to store various types of data therein. More specifically, the storage 120 is configured to store therein the diagnosis and treatment data received from the systems. For example, the storage 120 is realized by using a semiconductor memory element such as a Random Access Memory (RAM) or a flash memory, or a hard disk, an optical disk, or the like. The storage 120 is an example of a means for realizing a storage unit.

The input interface 130 is connected the processing circuitry 150 and is configured to receive an input operation of any of various types of instructions and various types of information, from an operator. More specifically, the input interface 130 is configured to convert the input operation received from the operator into an electrical signal and to output the electrical signal to the processing circuitry 150. For example, the input interface 130 is realized by using a trackball, a switch button, a mouse, a keyboard, a touch-pad on which input operations are performed by touching an operation surface thereof, a touch-screen in which a display screen and a touch-pad are integrated together, and/or a contactless input circuit using an optical sensor, and an audio input circuit or the like. In the present disclosure, the input interface 130 does not necessarily have to include a physical operation component part such as the mouse, the keyboard, and/or the like. For instance, examples of the input interface 130 include electrical signal processing circuitry configured to receive an electrical signal corresponding to an input operation from an external input device provided separately from the apparatus and to output the received electrical signal to a controlling circuit. The input interface 130 is an example of a means for realizing an input unit.

The display 140 is connected to the processing circuitry 150 and is configured to display various types of information and various types of images. More specifically, the display 140 is configured to convert the various types of information and the various types of images sent thereto from the processing circuitry 150, into a display-purpose electrical signal and to output the display-purpose electrical signal. For example, the display 140 is realized by using a liquid crystal monitor, a Cathode Ray Tube (CRT) monitor, a touch panel, or the like. The display 140 is an example of a means for realizing a display unit.

The processing circuitry 150 is configured to control constituent elements of the medical information processing apparatus 100 in response to the input operation received from the operator via the input interface 130. More specifically, the processing circuitry 150 is configured to store the diagnosis and treatment data output from the NW interface 110 into the storage 120. Further, the processing circuitry 150 is configured to read any of the diagnosis and treatment data from the storage 120 and to cause the display 140 to display the read data. For example, the processing circuitry 150 is realized by using a processor.

An overall configuration of the medical information processing apparatus 100 according to the present embodiment has thus been explained. The medical information processing apparatus 100 according to the present embodiment structured as described above is configured to make it possible for the operator (e.g., a medical doctor) to easily understand diagnosis and treatment actions and the state of the subject which the operator wishes to check.

More specifically, according to the present embodiment, the storage 120 stores therein an integrated diagnosis and treatment database (DB) including the various types of diagnosis and treatment data obtained from the specimen testing system 300, the radiation department system 400, and the electronic medical record system 500. In this situation, the diagnosis and treatment data stored in the integrated diagnosis and treatment DB includes pieces of information such as numerical values (measured values), images, and diagnosis and treatment records, as well as information indicating the recording dates/times of these pieces of information.

For example, the integrated diagnosis and treatment DB includes specimen test data, vital sign data, image data, prescription data, nursing record data, and the like. The specimen test data is diagnosis and treatment data related to specimen tests and obtained from the specimen testing system 300. The vital sign data is diagnosis and treatment data related to vital signs and obtained from the radiation department system 400. The image data is diagnosis and treatment data related to imaging tests and obtained from the radiation department system 400. The prescription data is diagnosis and treatment data related to prescriptions and obtained from the electronic medical record system 500. The nursing record data is diagnosis and treatment data related to nursing records and obtained from the electronic medical record system 500. In this situation, the diagnosis and treatment data stored in the integrated diagnosis and treatment DB may be the pieces of data themselves that were obtained from the specimen testing system 300, the radiation department system 400, and the electronic medical record system 500, may be data obtained by integrating the pieces of data obtained from these systems, or may be information generated for secondary use purposes.

Further, the storage 120 stores therein various types of tables (e.g., a display period/tally unit conversion table, a reference range table, a color code correspondence table, and a critical drug list table that are explained later) to be used by any of processing functions (explained later) included in the processing circuitry 150.

Further, in the present embodiment, the processing circuitry 150 includes a display controlling function 151, a detecting function 152, an obtaining function 153, a tallying function 154, and a calculating function 155. The display controlling function 151 is an example of the display controlling unit. The detecting function 152 is an example of a detecting unit. The obtaining function 153 is an example of an obtaining unit. The tallying function 154 is an example of the tallying unit. The calculating function 155 is an example of the calculating unit.

The display controlling function 151 is configured to display, in a time series, events of diagnosis and treatment actions performed on the subject during a designated display time period (hereinafter, "display period").

Figure 2:
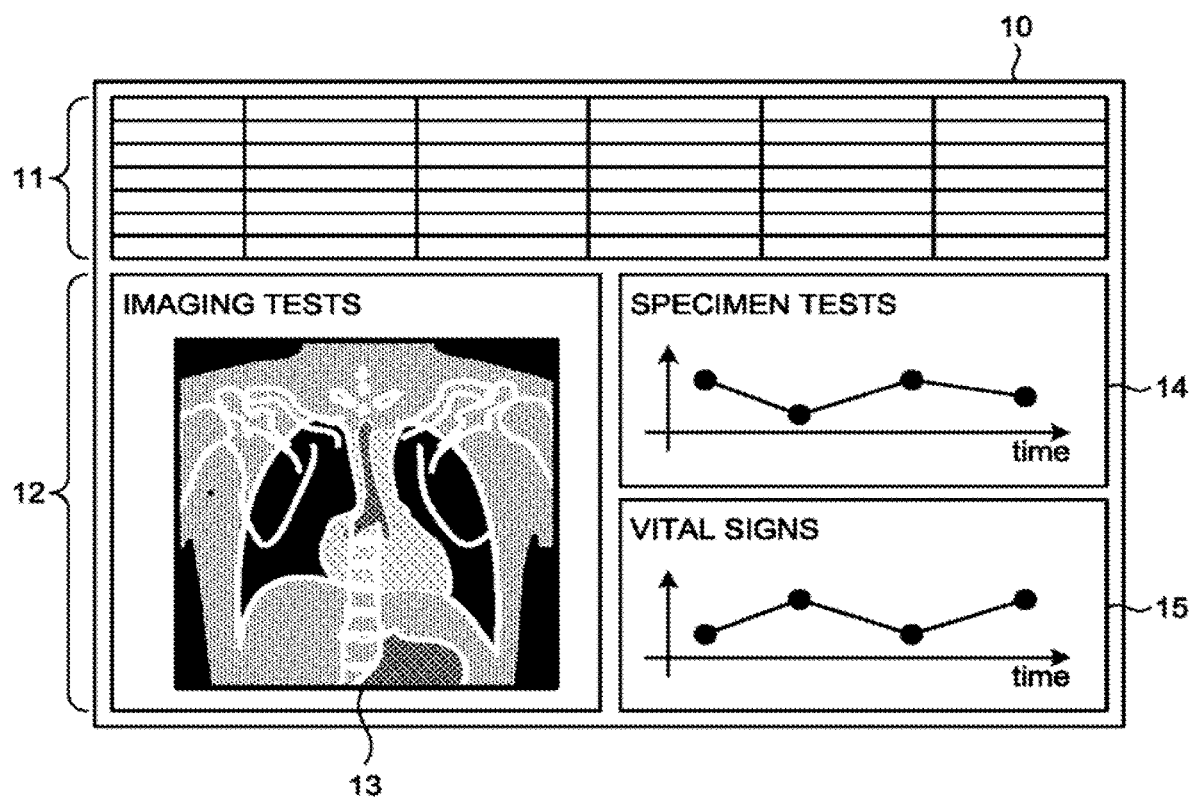
FIG. 2 is a drawing illustrating an example of a screen displayed by a display controlling function according to the present embodiment.

FIG. 2 is a drawing illustrating an example of a screen displayed by the display controlling function 151 according to the present embodiment. For example, as illustrated in FIG. 2, in response to a request from the operator, the display controlling function 151 causes the display 140 to display a screen 10 including a timeline display region 11 and a diagnosis and treatment data display region 12.

More specifically, in the timeline display region 11, the display controlling function 151 is configured to display, in a time series, the events of the diagnosis and treatment actions performed on the subject during the display period designated by the operator. For example, the display controlling function 151 displays icons corresponding to specifics of the events of the diagnosis and treatment actions performed on the subject during the display period, in such a manner that at least one icon is arranged for each of the tally units obtained by dividing the display period into sections arranged in a time series. For example, as the icons, the display controlling function 151 displays icons each expressing the specifics of a corresponding one of the events by using a figure, text, or a color. In the present example, the figure used in each of the icons is configured to symbolically express the specifics of the corresponding event.

Further, the display controlling function 151 receives, from the operator, an operation to designate a point in time or a time period within the display period displayed in the timeline display region 11 and further arranges detailed information indicating the specifics of the diagnosis and treatment data to be displayed in the diagnosis and treatment data display region 12, with respect to one or more events of diagnosis and treatment actions performed either at the designated point in time or during the designated time period. In that situation, the display controlling function 151 refers to the integrated diagnosis and treatment DB in the storage 120, obtains the diagnosis and treatment data related to the one or more events of the diagnosis and treatment actions performed either at the designated point in time or during the designated time period, and displays the detailed information indicating the specifics of the obtained diagnosis and treatment data in the diagnosis and treatment data display region 12.

For example, the display controlling function 151 refers to the image data included in the integrated diagnosis and treatment DB and displays, in the diagnosis and treatment data display region 12, a medical image 13 related to an imaging test performed either at the designated point in time or during the designated time period. Further, for example, the display controlling function 151 refers to the specimen test data included in the integrated diagnosis and treatment DB and displays, in the diagnosis and treatment data display region 12, a graph 14 indicating changes in measured values related to one or more specimen tests performed either at the designated point in time or during the designated time period. Further, for example, the display controlling function 151 refers to the vital sign data included in the integrated diagnosis and treatment DB and displays, in the diagnosis and treatment data display region 12, a graph 15 indicating changes in measured values related to vital signs taken either at the designated point in time or during the designated time period.

FIG. 3 is a drawing illustrating an example of information displayed in the timeline display region 11 by the display controlling function 151 according to the present embodiment. For example, as illustrated in FIG. 3, the display controlling function 151 displays, in the timeline display region 11, a panel 16 having a matrix formation in which the display period designated by the operator is kept in correspondence with the columns, while the types of events are kept in correspondence with the lines.

Further, the display controlling function 151 is configured to refer to the integrated diagnosis and treatment DB in the storage 120 and to display icons expressing the specifics of the events and being arranged in the corresponding sections of the panel 16, on the basis of the diagnosis and treatment data related to the events of the diagnosis and treatment actions performed either at the designated point in time or during the designated time period. In that situation, for example, the display controlling function 151 displays the events in the timeline display region 11 with respect to the display period determined in advance. For example, the display controlling function 151 displays the events with respect to either the entire time period containing the diagnosis and treatment data or a time period from the current date/time up to two weeks earlier.

Further, the display controlling function 151 is configured to receive an operation to change the display period from the operator. For example, the display controlling function 151 receives, as the operation to change the display period, an operation to turn the wheel of a mouse or an operation to zoom in or zoom out on a touch-screen included in a tablet terminal. Further, in response to the received operation, the display controlling function 151 changes the range of the display period displayed in the timeline display region 11. As a result, the operator is able to designate an arbitrary time unit or range as the display period.

Further, the display controlling function 151 is configured to receive an operation performed on any of the events displayed in the timeline display region 11. For example, when having received an operation to designate an icon related to image data, the display controlling function 151 displays, in the timeline display region 11, a list 17 of imaging tests performed during the time period corresponding to the designated icon. In this situation, the number of imaging tests displayed in the list 17 varies depending on the number of imaging tests performed during the time period corresponding to the designated icon. Further, when having received the operation, the display controlling function 151 displays, in the diagnosis and treatment data display region 12, a medical image related to an imaging test selected from the list 17.

The detecting function 152 is configured to detect that the display period displayed by the display controlling function 151 has been changed. For example, when the operator has performed an operation to change the display period, the detecting function 152 detects that the display period has been changed.

The obtaining function 153 is configured to obtain the display period displayed by the display controlling function 151. Further, when the detecting function 152 detects that the display period has been changed, the obtaining function 153 is configured to obtain the display period after the change. For example, the obtaining function 153 obtains, as the display period, a time period expressed with year/month/day and times of the day such as "2017 Apr. 11, 10:00 to 2017 Jul. 11, 10:00".

The tallying function 154 is configured to tally, as an index value, numerical values either extracted or calculated on the basis of information about the events of the diagnosis and treatment actions performed on the patient during the display period, for each of tally units resulting from dividing the display period obtained by the obtaining function 153 into sections arranged in a time series. Further, when the detecting function 152 detects that the display period has been changed, the tallying function 154 is configured to re-tally the index values on the basis of the display period after the change obtained by the obtaining function 153.

In the present embodiment, as an example, the tallying function 154 is configured to tally, as the index value, values each indicating a degree of a change in either the diagnosis and treatment actions or the state of the subject.

More specifically, the tallying function 154 refers to the display period/tally unit conversion table stored in the storage 120 and determines the tally units used for dividing the display period into the sections arranged in a time series.

FIG. 4 is a drawing illustrating an example of the display period/tally unit conversion table referred to by the tallying function 154 according to the present embodiment. For example, as illustrated in FIG. 4, the display period/tally unit conversion table stores therein information in which display periods are kept in correspondence with tally units. In this situation, as the display periods, a plurality of time periods of which the time lengths gradually vary are set, e.g., "3 or more years", "6 months to 3 years", "2 months to 6 months", "2 weeks to 2 months", "5 days to 2 weeks", "1 day to 5 days", and so on. Further, as the tally units, units of time used for dividing each of the display periods into sections arranged in a time series are set, e.g., "1 year", "1 month", "1 week", "3 days", "1 day", "6 hours", and so on.

Further, the tallying function 154 is configured to divide the display period into the sections corresponding to the tally units determined with reference to the display period/tally unit conversion table.

FIG. 5 is a drawing illustrating an example of the display period dividing process performed by the tallying function 154 according to the present embodiment. In this situation, FIG. 5 illustrates an example in which the display period is "2017 Apr. 11, 10:00 to 2017 Jul. 11, 10:00", while the tally unit determined with reference to the display period/tally unit conversion table is "1 week".

In that situation, for example, as illustrated in FIG. 5, the tallying function 154 divides the display period "2017 Apr. 11, 10:00 to 2017 Jul. 11, 10:00" into sections each representing one week, such as "2017 Apr. 11, 10:00 to 2017 Apr. 18, 10:00", "2017 Apr. 18, 10:00 to 2017 Apr. 25, 10:00", "2017 Apr. 25, 10:00 to 2017 May 2, 10:00", . . . , and "2017 Jul. 4, 10:00 to 2017 Jul. 11, 10:00".

After that, for each of the tally units resulting from the dividing process, the tallying function 154 tallies the index value indicating a degree of a change in either the diagnosis and treatment actions or the state of the subject.

In the present embodiment, the tallying function 154 tallies, as the index value, abnormality values each indicating an abnormality in either the diagnosis and treatment actions or the state of the subject. In this situation, the abnormality values are numerical values each of which indicates a certain abnormality related to either the diagnosis and treatment actions or the state of the subject and which are defined in correspondence with the types of events of the diagnosis and treatment actions. In the following sections, an example will be explained in which values are tallied with respect to vital signs, specimen tests, imaging tests, prescriptions, and nursing records.

For example, with respect to the vital signs, the tallying function 154 tallies the number of times when a measured value fell outside a reference range as an abnormality value. In this situation, the tallying function 154 tallies the number of times when a measured value fell outside the reference range, by referring to the vital sign data included in the integrated diagnosis and treatment DB and the reference range table stored in the storage 120.

FIG. 6 is a drawing illustrating an example of the vital sign data referred to by the tallying function 154 according to the present embodiment. For example, as illustrated in FIG. 6, the vital sign data is information in which patient IDs, types of vital signs, measured dates/times, and measured values are kept in correspondence with one another. In this situation, as the patient IDs, pieces of identification information uniquely identifying the subjects are set. Further, as the types of vital signs, pieces of information indicating various types of vital signs (e.g., pulse rates, blood pressure values, body temperatures, etc.) are set. Further, as the measured dates/times, the dates/times on which the vital signs were measured from the corresponding subjects are set. Further, as the measured values, the measured values of the vital signs are set.

FIG. 7 is a drawing illustrating an example of the reference range table referred to by the tallying function 154 according to the present embodiment. For example, as illustrated in FIG. 7, the reference range table is information in which types of vital signs and reference ranges are kept in correspondence with each other. In this situation, as the types of vital signs, pieces of information indicating various types of vital signs (e.g., pulse rates, blood pressure values, body temperatures, etc.) are set. Further, as the reference ranges, reference ranges related to the types of vital signs are set.

More specifically, by referring to the reference range table, the tallying function 154 obtains a reference range for each of the various types of vital signs. Further, by referring to the measured dates/times and the measured values included in the vital sign data, the tallying function 154 tallies, for each of the time periods in the tally units, the number of pieces of data of which the measured value fell outside the reference range.

FIG. 8 is a drawing illustrating an example of the tallying process related to the vital signs and performed by the tallying function 154 according to the present embodiment. For example, as illustrated in FIG. 8, with respect to the vital signs, the tallying function 154 tallies the number of pieces of data of which the measured value fell outside the reference range, for each of the tally units obtained by dividing the display period "2017 Apr. 11, 10:00 to 2017 Jul. 11, 10:00" into the sections each representing one week.

Further, as another example, with respect to the specimen tests, the tallying function 154 tallies the number of times when the measure value fell outside the reference range as an abnormality value. In this situation, by referring to the specimen test data included in the integrated diagnosis and treatment DB and the reference range table for the specimen tests stored in the storage 120, the tallying function 154 tallies the number of times when the measured value fell outside the reference range, by using the same method as the method used for the vital signs.

Further, as yet another example, with respect to the imaging tests, the tallying function 154 tallies the number of types of imaging tests that were performed as an abnormality value. In this situation, by referring to the image data included in the integrated diagnosis and treatment DB, the tallying function 154 tallies the number of types of imaging tests that were performed.

FIG. 9 is a drawing illustrating an example of the image data referred to by the tallying function 154 according to the present embodiment. For example, as illustrated in FIG. 9, the image data is information in which patient IDs, dates/times, and pieces of data are kept in correspondence with one another. In this situation, as the patient IDs, pieces of identification information uniquely identifying the subjects are set. Further, as the dates/times, the dates/times on which the imaging tests were performed on the corresponding subjects are set. Further, as the pieces of data, pieces of Digital Imaging and Communications in Medicine (DICOM) data of the images used in the imaging tests are set. In this situation, each of the pieces of DICOM data includes a DICOM tag (0008,0060) set with information indicating the type of modality (a medical image diagnosis apparatus) used for taking the image.

More specifically, the tallying function 154 tallies the number of types of modality for each of the time periods in the tally units, by referring to the dates/times included in the image data and the DICOM tag (0080,0060) appended to each of the pieces of DICOM data.

FIG. 10 is a drawing illustrating an example of the tallying process related to the imaging tests and performed by the tallying function 154 according to the present embodiment. For example, as illustrated in FIG. 10, with respect to the imaging tests, the tallying function 154 tallies the number of types of modality for each of the tally units obtained by dividing the display period "2017 Apr. 11, 10:00 to 2017 Jul. 11, 10:00" into the sections each representing one week.

Alternatively, for example, instead of tallying the number of types of modality, the tallying function 154 may tally the number of types of Service Object Pair (SOP) classes for each of the time periods in the tally units, by referring to the dates/times included in the image data and the DICOM tag (0008,0016) appended to each of the pieces of DICOM data.

FIG. 11 is a drawing illustrating examples of the DICOM tag (0008,0016) referred to by the tallying function 154 according to the present embodiment. For example, as illustrated in FIG. 11, the DICOM tag (0008,0016) appended to DICOM data is set with information (a Unique Identifier [UID] name) indicating any one of various SOP classes (sets each made up of an object and a service) defined in correspondence with Unique Identifiers (UIDs) by a DICOM standard.

Further, for example, with respect to the prescriptions, the tallying function 154 tallies the number of types of drugs as an abnormality value. In this situation, by referring to the prescription data included in the integrated diagnosis and treatment DB, the tallying function 154 tallies the number of types of drugs.

FIG. 12 is a drawing illustrating an example of the prescription data referred to by the tallying function 154 according to the present embodiment. For example, as illustrated in FIG. 12, the prescription data is information in which patient IDs, dates/times, and pieces of data are kept in correspondence with one another. In this situation, as the patient IDs, pieces of identification information uniquely identifying the subjects are set. Further, as the dates/times, the dates/times on which the drugs were prescribed for the corresponding subjects are set. Further, as the pieces of data, pieces of information indicating the types of drugs that were prescribed are set.

More specifically, by referring to the dates/times and the pieces of data included in the prescription data, the tallying function 154 tallies the number of types of drugs, for each of the time periods in the tally units.

FIG. 13 is a drawing illustrating an example of the tallying process related to the prescriptions and performed by the tallying function 154 according to the present embodiment. For example, as illustrated in FIG. 13, with respect to the prescriptions, the tallying function 154 tallies the number of types of drugs, for each of the tally units obtained by dividing the display period "2017 Apr. 11, 10:00 to 2017 Jul. 11, 10:00" into the sections each representing one week.

Further, for example, with respect to the nursing records, the tallying function 154 tallies the number of nursing records each written with at least one negative expression as an abnormality value. In this situation, by referring to the nursing record data included in the integrated diagnosis and treatment DB, the tallying function 154 tallies the number of nursing records each written with at least one negative expression.

FIGS. 14 and 15 are drawings illustrating examples of the nursing record data referred to by the tallying function 154 according to the present embodiment. For example, as illustrated in FIG. 14, the nursing record data is information in which patient IDs, dates/times, and pieces of data are kept in correspondence with one another. In this situation, as the patient IDs, pieces of identification information uniquely identifying the subjects are set. Further, as the dates/times, the dates/times on which the nursing records related to the corresponding subjects were generated are set. Further, as the pieces of data, pieces of information indicating the content of the generated nursing records are set.

For example, as illustrated in FIG. 15, as the data in the nursing record data, results of nursing activities performed on the subjects are set by using a text format. The example in FIG. 15 illustrates four nursing records generated at 8:15, 8:35, 9:03, and 9:21.

More specifically, by referring to the dates/times and the pieces of data included in the nursing record data, the tallying function 154 tallies the number of nursing records each written with at least one negative expression, for each of the time periods in the tally units.

In this situation, for example, the tallying function 154 judges whether or not each of the corresponding nursing records is written with at least one negative expression, by performing a text analysis on the contents of the nursing records included in the pieces of data in the nursing record data. In this situation, it is possible to use any of various types of publicly-known methods as the method for performing the text analysis.

For example, the tallying function 154 uses dictionary data in which positive index values are kept in correspondence with words defined as positive expressions (e.g., "really", "enjoyable", etc.) and words defined as negative expressions (e.g., "a cold", "sad", etc.). In this situation, the positive index values are indices each indicating a degree of being positive. For example, with respect to the words defined as the positive expressions, a positive numerical value of which the magnitude is varied depending on the degree of being positive is set. With respect to the words defined as the negative expressions, a negative numerical value of which the magnitude is varied depending on the degree of being positive is set. In that situation, the tallying function 154 searches for the words registered in the dictionary data, by referring to the nursing records included in the pieces of data in the nursing record data. Further, the tallying function 154 calculates a sum of the positive index values kept in correspondence with the searched words, and when the total value is a negative value, the tallying function 154 determines that the corresponding nursing record is written with negative expressions.

FIG. 16 is a drawing illustrating an example of the tallying process related to the nursing records and performed by the tallying function 154 according to the present embodiment. For example, as illustrated in FIG. 16, with respect to the nursing records, the tallying function 154 tallies the number of nursing records written with at least one negative expressions, for each of the tally units obtained by dividing the display period "2017 Apr. 11, 10:00 to 2017 Jul. 11, 10:00" into the sections each representing one week.

Alternatively, for example, with respect to the nursing records, the tallying function 154 may tally the number of characters written in the nursing records as an abnormality value. More specifically, the tallying function 154 may tally the number of characters written in the nursing records, by referring to the dates/times and the pieces of data included in the nursing record data.

FIG. 17 is a drawing illustrating another example of the tallying process related to the nursing records and performed by the tallying function 154 according to the present embodiment. For example, as illustrated in FIG. 17, with respect to the nursing records, the tallying function 154 may tally the number of characters written in the nursing records, for each of the tally units obtained by dividing the display period "2017 Apr. 11, 10:00 to 2017 Jul. 11, 10:00" into the sections each representing one week.

The calculating function 155 is configured to calculate a piece of context information relatively indicating either the diagnosis and treatment actions or the state of the subject in each of the tally units, by comparing, with one another, the index values tallied by the tallying function 154 for the tally units, and is further configured to display the pieces of context information so as to be kept in association with the events of the diagnosis and treatment actions. Further, when the detecting function 152 detects that the display period has been changed, the calculating function 155 is configured to dynamically display context information by re-calculating the context information on the basis of re-tallied index values.

In this situation, each of the pieces of context information is information indicating circumstances, backgrounds, and/or situations of the changes in either the diagnosis and treatment actions or the state of the subject.

FIGS. 18 to 24 are drawings illustrating examples of the context information calculating and displaying processes performed by the calculating function 155 according to the present embodiment. In the following sections, an example will be explained in which, as a piece of context information, the calculating function 155 calculates and displays a color corresponding to a tallied value for each of the tally units.

Figure 18:
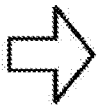
FIG. 18 is a drawing illustrating an example of context information calculating and displaying processes performed by a calculating function according to the present embodiment.

For example, as illustrated in FIG. 18, the calculating function 155 at first normalizes the tallied value for each of the tally units, on the basis of maximum and minimum values among the tallied values obtained by the tallying function 154, for each of the types of events.

$$Y = \frac{X - x_{min}}{x_{max} - x_{min}}$$

In the expression above, Y denotes a tallied value that has been normalized, whereas X denotes a tallied value for any one of the tally units. Further, $x_{min}$ denotes the minimum value among the tallied values for the type of events, whereas $x_{max}$ denotes the maximum value among the tallied values for the type of events. In this situation, when $x_{max}=x_{min}$ is satisfied, Y=0 is true. Further, when no diagnosis or treatment action was taken during the time period of a tally unit, no value shall be set to Y.

After that, the calculating function 155 assigns a color code to each of the normalized tallied values, by referring to the color code correspondence table stored in the storage 120.

FIG. 19 is a drawing illustrating an example of the color code correspondence table referred to by the calculating function 155 according to the present embodiment. For example, as illustrated in FIG. 19, the color code correspondence table provides information in which normalized values, colors, and color codes are kept in correspondence with one another. In the present example, as the normalized values, ranges of normalized tallied values are set. Further, as the colors, information (e.g., blue, yellow, red, etc.) indicating colors each assigned to corresponding normalized values are set. Further, as the color codes, codes uniquely indicating the colors are set.

Figure 20:
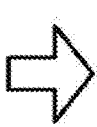
FIG. 20 is a drawing illustrating yet another example of the context information calculating and displaying processes performed by the calculating function according to the present embodiment.

For example, as illustrated in FIG. 20, the calculating function 155 assigns a color code to each of the normalized tallied values, by referring to the normalized values and the color codes included in the color code correspondence table.

Figure 21:
FIG. 21 is a drawing illustrating yet another example of the context information calculating and displaying processes performed by the calculating function according to the present embodiment.

Further, for example, as illustrated in FIG. 21, the calculating function 155 displays the color in each of the sections of the panel 16 displayed in the timeline display region 11, on the basis of the color codes assigned to the tallied values. In the example in FIG. 21, the icons supposed to be displayed in the panel 16 are omitted from the drawing.

Figure 22:
FIG. 22 is a drawing illustrating yet another example of the context information calculating and displaying processes performed by the calculating function according to the present embodiment.

Also, for example, as illustrated in FIG. 22, in addition to displaying the colors, the calculating function 155 may further display the tallied value tallied by the tallying function 154 in each of the sections of the panel 16 displayed in the timeline display region 11.

Figure 23:
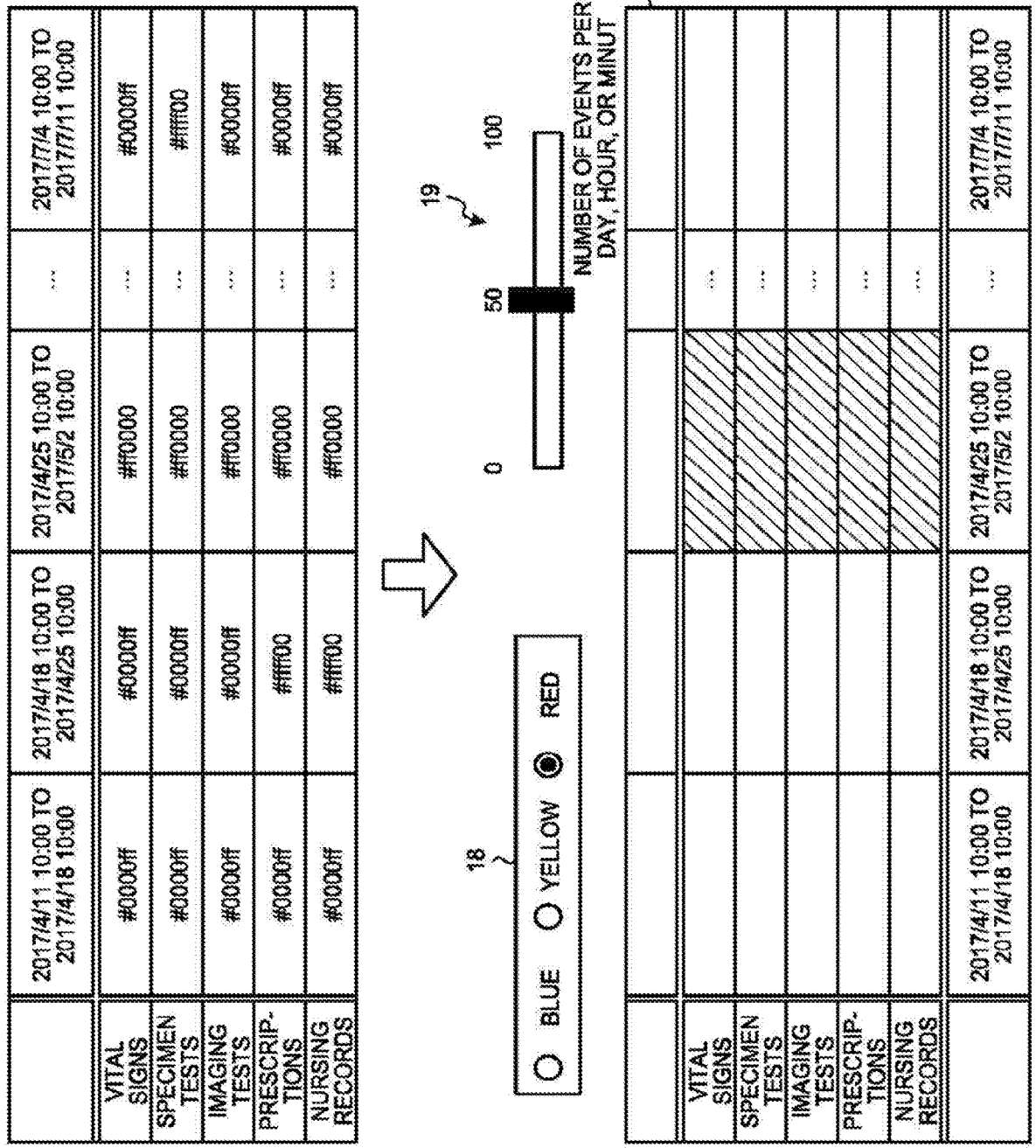
FIG. 23 is a drawing illustrating yet another example of the context information calculating and displaying processes performed by the calculating function according to the present embodiment.

Alternatively, for example, as illustrated in FIG. 23, by receiving an operation performed by the operator on any of radio buttons 18 corresponding to the colors and being displayed together with the panel 16, the calculating function 155 may display a color only in such sections to which the selected color is assigned. Alternatively, by receiving an operation performed by the operator on a slide bar 19 displayed together with the panel 16, the calculating function 155 may display a color only in such sections of which the tallied value is equal to or larger than a threshold value. With any of these arrangements, it is possible to display the information while placing an emphasis on a specific piece of information.

Figure 24:
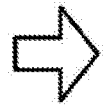
FIG. 24 is a drawing illustrating yet another example of the context information calculating and displaying processes performed by the calculating function according to the present embodiment.

Alternatively, for example, as illustrated in FIG. 24, the calculating function 155 may further display arrow-shaped graphic elements 20 each indicating that the tallied value tallied by the tallying function 154 changed, in the panel 16 displayed in the timeline display region 11. In that situation, for example, the calculating function 155 may change the thickness of the arrow-shaped graphic elements 20 in accordance with the amounts of change in the tallied values. Further, for example, the calculating function 155 may display an arrow-shaped graphic element 20 only in such a section where there was a change in the tallied value.

The processing functions of the processing circuitry 150 have thus been explained. In this situation, as explained above, the processing circuitry 150 is realized by using a processor, for example. In that situation, the processing functions of the processing circuitry 150 are stored in the storage 120 in the form of computer-executable programs. Further, the processing circuitry 150 is configured to realize the functions corresponding to the programs by reading and executing the programs from the storage 120. In other words, the processing circuitry 150 that has read the programs has the functions illustrated within the processing circuitry 150 in FIG. 1. Although FIG. 1 illustrates the example in which the processing functions are realized by the single processor, it is also acceptable to structure the processing circuitry by combining together a plurality of independent processors so that the functions are realized as a result of the processors executing the programs. Further, the processing functions of the processing circuitry 150 may be realized as being integrated into a single piece of processing circuitry or as being distributed among a plurality of pieces of processing circuitry, as appropriate. Further, although FIG. 1 illustrates the example in which the single storage (i.e., the storage 120) stores therein the programs corresponding to the processing functions, another arrangement is also acceptable in which two or more storages are arranged in a distributed manner, so that the processing circuitry reads a corresponding one of the programs from each individual storage.

Figure 25:
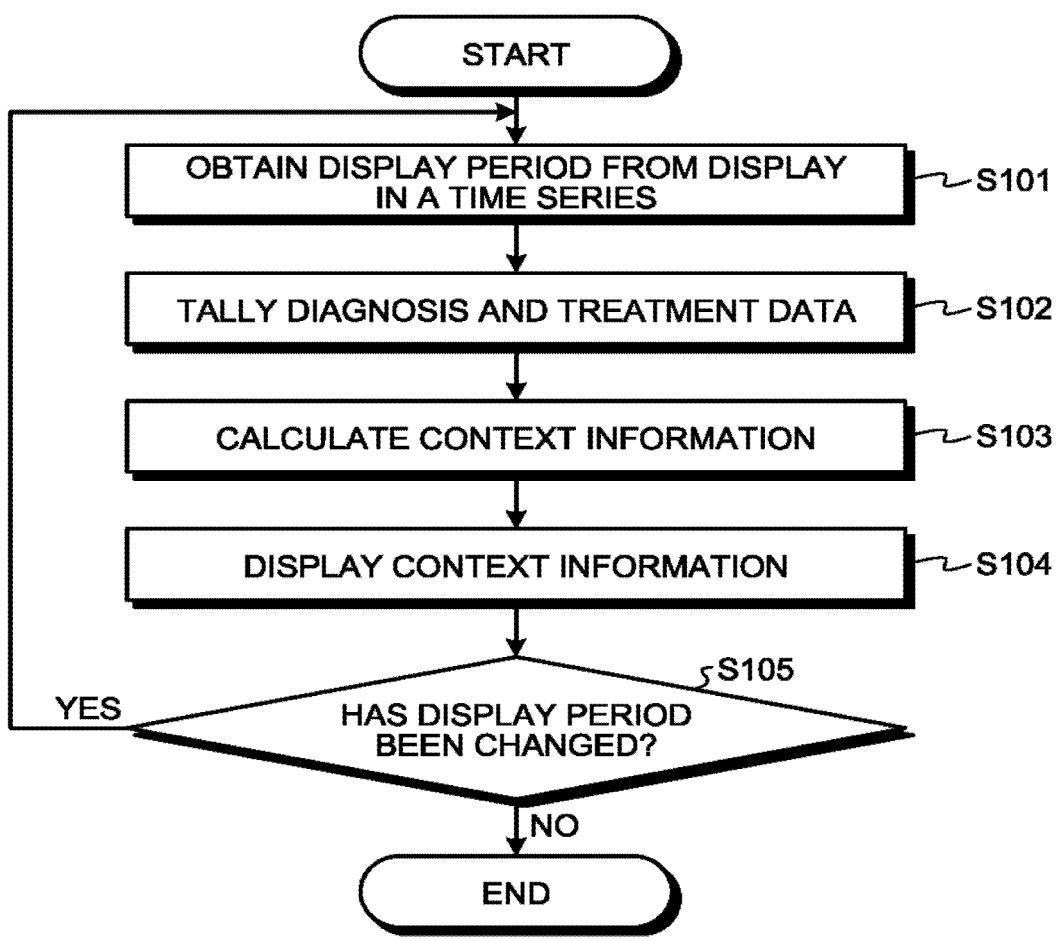
FIG. 25 is a flowchart illustrating a processing procedure in a process performed by a medical information processing apparatus according to the present embodiment.

FIG. 25 is a flowchart illustrating a processing procedure in a process performed by the medical information processing apparatus 100 according to the present embodiment. For example, as illustrated in FIG. 25, in the present embodiment, in response to a request from the operator, the processing circuitry 150 displays the screen 10 including the timeline display region 11 and obtains the display period displayed in the timeline display region 11 (Obtain the display period from the display in a time series: step S101).

Subsequently, with respect to the events of the diagnosis and treatment actions performed on the subject during the display period, the processing circuitry 150 tallies an index value indicating a degree of a change in either diagnosis and treatment actions or the state of the subject, for each of the tally units obtained by dividing the display period into sections arranged in a time series (Tally the diagnosis and treatment data: step S102).

After that, by comparing the index values tallied for the tally units with one another, the processing circuitry 150 calculates a piece of context information relatively indicating either the diagnosis and treatment actions or the state of the subject in the tally unit (Calculate the context information: step S103) and further displays the calculated pieces of context information so as to be kept in association with the events of the diagnosis and treatment actions (Display the context information: step S104).

Subsequently, when it is detected that the display period has been changed (step S105: Yes), the processing circuitry 150 obtains the display period after the change (step S101), re-tallies index values on the basis of the display period after the change (step S102), and dynamically displays context information by re-calculating the context information on the basis of the re-tallied index values (step S104).

On the contrary, when it is not detected that the display period has been changed (step S105: No), the processing circuitry 150 ends the process.

In this situation, the process at step S101 described above is realized, for example, as a result of the processing circuitry 150 reading and executing predetermined programs corresponding to the display controlling function 151 and the obtaining function 153 from the storage 120. Further, the process at step S102 described above is realized, for example, as a result of the processing circuitry 150 reading and executing a predetermined program corresponding to the tallying function 154 from the storage 120. Further, the process at steps S103 and S104 described above is realized, for example, as a result of the processing circuitry 150 reading and executing a predetermined program corresponding to the calculating function 155 from the storage 120. Further, the process at step S105 described above is realized, for example, as a result of the processing circuitry 150 reading and executing a predetermined program corresponding to the detecting function 152 from the storage 120.

It is possible to carry out the embodiment described above by applying a modification thereto as appropriate.

For example, in the embodiment described above, the example is explained in which the tallying function 154 tallies the abnormality values in either the diagnosis and treatment actions or the state of the subject as the index values; however, possible embodiments are not limited to this example. For instance, the tallying function 154 may tally the number of critical events defined in advance, as an index value. In this situation, the critical events denote, for example, tests, procedures, and the like having a possibility of greatly involving a change in the state of the subject.

In one example, with respect to critical prescriptions defined in advance, the tallying function 154 tallies the number of types of drugs as an index value. In this situation, the tallying function 154 tallies the number of types of drugs, by referring to the prescription data included in the integrated diagnosis and treatment DB and the critical drug list table stored in the storage 120.

FIG. 26 is a drawing illustrating an example of the critical drug list table referred to by the tallying function 154 according to a modification example of the present embodiment. For example, as illustrated in FIG. 26, the critical drug list table is information including critical drugs. In this situation, as the critical drugs, information indicating critical types of drugs defined in advance is set.

More specifically, the tallying function 154 identifies the critical types of drugs defined in advance, by referring to the critical drug list table. Further, with respect to the critical types of drugs, the tallying function 154 tallies the number of types of drugs for each of the time periods in the tally units, by referring to the dates/times and pieces of data included in the prescription data.

Alternatively, for example, the tallying function 154 may tally the number of critical events defined by the operator, as an index value. In that situation, the integrated diagnosis and treatment DB includes critical event data generated by the operator.

FIG. 27 is a drawing illustrating an example of the critical event data referred to by the tallying function 154 according to another modification example of the present embodiment. For example, as illustrated in FIG. 27, the critical event data is information in which patient IDs, dates/times, and specifics of events are kept in correspondence with one another. In this situation, as the patient IDs, pieces of identification information uniquely identifying the subjects are set. Further, as the dates/times, the dates/times on which the critical events occurred for the corresponding subjects are set. Further, as the specifics of the events, pieces of information indicating specifics of the critical events (e.g., hospitalization, a sudden change in the subject's condition, stabilization of the subject's condition) are set.

More specifically, with respect to each of the time periods in the tally units, the tallying function 154 tallies the number of critical events, by referring to the dates/times and the specifics of the events included in the critical event data.

FIG. 28 is a drawing illustrating an example of the tallying process related to the critical events and performed by the tallying function 154 according to yet another modification example of the present embodiment. For example, as illustrated in FIG. 28, with respect to the critical events, the tallying function 154 tallies the number of critical events (e.g., sudden changes in the subject's condition and stabilization of the subject's condition) for each of the tally units obtained by dividing the display period "2017 Jul. 11, 10:00 to 2017 Jul. 11, 10:00" into the sections each representing one week.

Further, for instance, in the embodiment above, the example is explained in which, as the context information, the calculating function 155 calculates and displays the colors corresponding to the tallied values obtained in correspondence with the tally units; however, possible embodiments are not limited to this example. For instance, as the context information, the calculating function 155 may calculate and display information indicating differences in the index values among the tally units.

Figure 29:
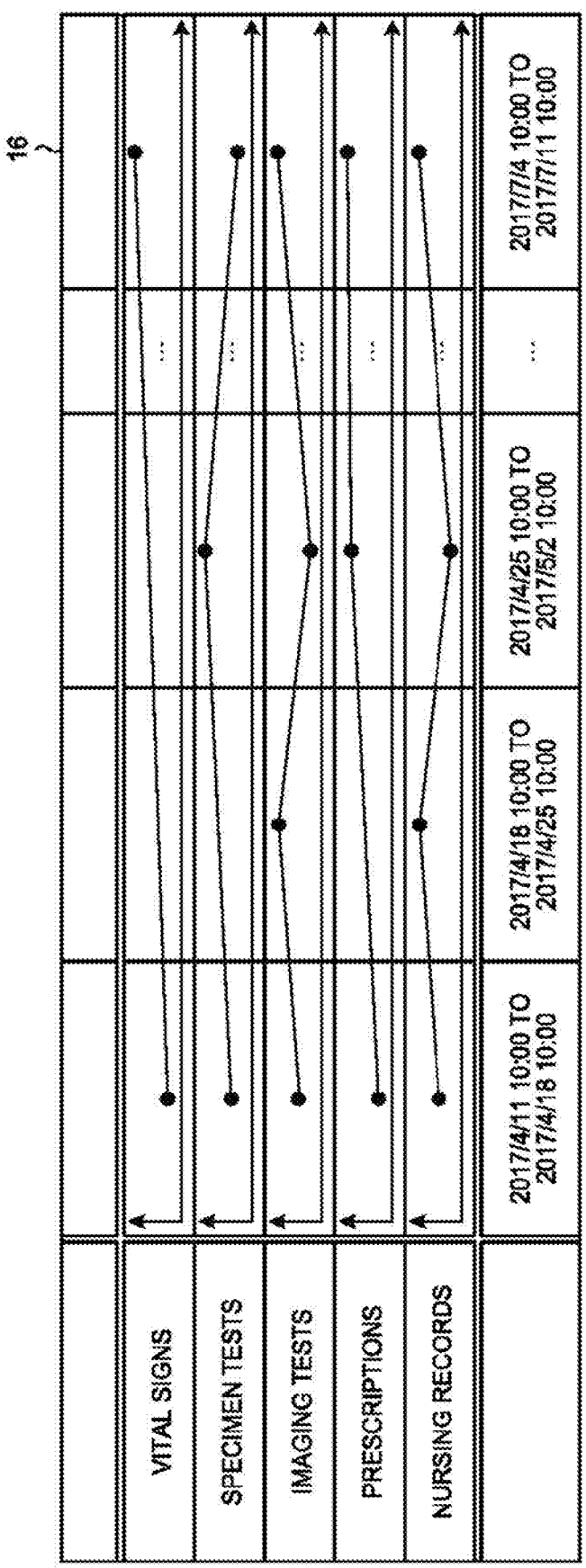
FIG. 29 is a drawing illustrating an example of context information calculating and displaying processes performed by a calculating function according to yet another modification example of the present embodiment.

FIG. 29 is a drawing illustrating an example of the context information calculating and displaying processes performed by the calculating function 155 according to yet another modification example of the present embodiment. For example, as illustrated in FIG. 29, for each of the types of events, the calculating function 155 displays a line graph indicating difference values in relation to immediately preceding and immediately following tallied values, in the panel 16 displayed in the timeline display region 11. In this situation, for example, instead of using the line graph, the calculating function 155 may display the difference values by using colors or may emphasize the display in only such sections that each exhibit a large difference value.

Further, for example, the calculating function 155 may arrange the pieces of context information corresponding to the events to be displayed, side by side while the time sequences thereof are aligned, with pieces of information indicating the number of occurrences of events (how many events occurred) with respect to the events displayed in a time series.

Figure 30:
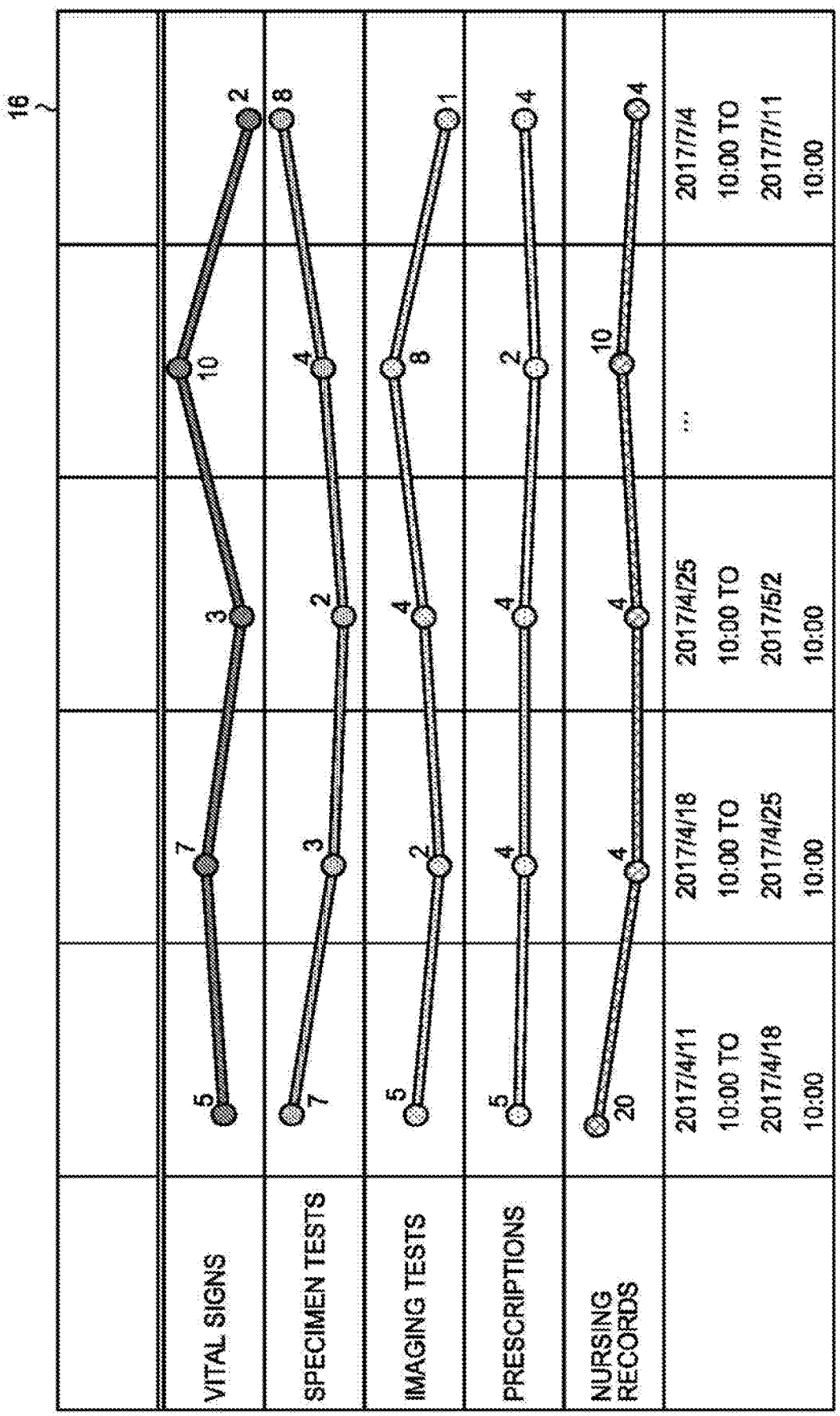
FIG. 30 is a drawing illustrating an example of a context information displaying process performed by a calculating function according to yet another modification example of the present embodiment.

FIG. 30 is a drawing illustrating an example of the context information displaying process performed by the calculating function according to yet another modification example of the present embodiment. For example, as illustrated in FIG. 30, for each of the types of events, the calculating function 155 displays a line graph indicating the difference values in relation to immediately preceding and immediately following tallied values, in the panel 16 displayed in the timeline display region 11. Further, in that situation, the calculating function 155 displays the number of events for each of the time periods in the tally units, while the time sequences thereof are aligned with those of the line graph.

Further, for example, the calculating function 155 may realize the display by replacing the pieces of context information corresponding to the events, with the pieces of information indicating the number of occurrences of events with respect to the events displayed in a time series. For example, the calculating function 155 may realize the display while switching between the line graph and the number of events for each of the time periods in the tally units illustrated in FIG. 30, in response to an instruction from the operator.

As explained above, according to the present embodiment, the display controlling function 151 is configured to display, in a time series, the events of the diagnosis and treatment actions performed on the subject during the designated display period. Further, for each of the tally units obtained by dividing the display period into sections arranged in a time series, the tallying function 154 is configured to tally the numerical values either extracted or calculated on the basis of the information about the events, as the index value. Further, the calculating function 155 is configured to calculate the pieces of context information each relatively indicating either the diagnosis and treatment actions or the state of the subject in a corresponding one of the tally units, by comparing the index values tallied for the tally units with one another, so that the pieces of context information are displayed while being kept in association with the events of the diagnosis and treatment actions.

For example, in the present embodiments, the tallying function 154 is configured to tally the values each indicating a degree of a change in either the diagnosis and treatment actions or the state of the subject, as the index values. With this arrangement, the pieces of context information each relatively indicating either the diagnosis and treatment actions or the state of the subject in a corresponding one of the tally units are displayed in accordance with the degrees (large/small; many/a few) of the changes in either the diagnosis and treatment actions performed on the subject or the state of the subject. Accordingly, the operator (e.g., a medical doctor) is able to understand, at a glance, circumstances, backgrounds, and situations of the changes in either the diagnosis and treatment actions or the state of the subject.

Consequently, according to the present embodiments, the operator (e.g., a medical doctor) is able to easily understand the diagnosis and treatment actions and the state of the subject which the operator wishes to check.

For example, according to the present embodiments, because the context information is displayed to indicate the circumstances, the backgrounds, and the situations of the changes in the diagnosis and treatment actions and the state of the subject, the operator (e.g., a medical doctor) is able to understand the diagnosis and treatment actions and the state of the subject more easily than when another method is used by which the number of pieces of diagnosis and treatment data are simply displayed in a time series.

Further, for example, according to the present embodiments, the context information indicating the circumstances, the backgrounds, and the situations of the changes in the diagnosis and treatment actions and the state of the subject is displayed while being kept in association with the events of the diagnosis and treatment actions. Accordingly, the operator (e.g., a medical doctor) is able to understand the diagnosis and treatment actions and the state of the subject more easily than when another method is used by which a timeline and specifics of diagnosis and treatment data are displayed separately from each other.

Further, in the present embodiments, the detecting function 152 is configured to detect that the display period has been changed. Further, when it is detected that the display period has been changed, the tallying function 154 is configured to re-tally the index values on the basis of the display period after the change. The calculating function 155 is configured to dynamically display context information by re-calculating the context information on the basis of the re-tallied index values.

With these arrangements, the context information is dynamically displayed in accordance with the changes made to the display period. Accordingly, the operator (e.g., a medical doctor) is able to understand the circumstances, the backgrounds, and the situations of the changes in the diagnosis and treatment actions and the state of the subject more efficiently than when another method is used by which, for example, the units of time periods that can be displayed are limited.

In the embodiments described above, the example is explained in which the display controlling unit, the detecting unit, the obtaining unit, the tallying unit, and the calculating unit of the present disclosure are realized by the display controlling function 151, the detecting function 152, the obtaining function 153, the tallying function 154, and the calculating function 155, respectively, that are included in the processing circuitry 150; however, possible embodiments are not limited to this example. For example, besides realizing the display controlling unit, the detecting unit, the obtaining unit, the tallying unit, and the calculating unit of the present disclosure by using the display controlling function 151, the detecting function 152, the obtaining function 153, the tallying function 154, and the calculating function 155 described in the embodiments, it is also acceptable to realize the functions by using only hardware or by using a combination of hardware and software.

The term "processor" used in the explanations above denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions thereof by reading and executing corresponding programs stored in the storage 120. In this situation, instead of saving the programs in the storage 120, it is also acceptable to directly incorporate the programs in the circuits of the processors. In that situation, the processors realize the functions thereof by reading and executing the programs incorporated in the circuits thereof. Further, the one or more processors in the present embodiments do not each necessarily have to be structured as a single circuit. It is also acceptable to structure one processor by combining together a plurality of independent circuits so as to realize the functions thereof.

In this situation, the programs executed by the one or more processors are provided as being incorporated, in advance, in a Read-Only Memory (ROM), a storage, or the like. Alternatively, the programs may be provided as being recorded on a computer-readable storage medium such as a Compact Disk Read-Only Memory (CD-ROM), a Flexible Disk (FD), a Compact Disk Recordable (CD-R), a Digital Versatile Disk (DVD), or the like, in a file in such a format that is either installable or executable for the devices. Further, the programs may be stored in a computer connected to a network such as the Internet, so as to be provided or distributed as being downloaded via the network. For example, each of the programs is structured with a module including the functional units described above. In the actual hardware, as a result of a CPU reading and executing the programs from a storage medium such as a ROM, the modules are loaded into a main storage device so as to be generated in the main storage device.

According to at least one aspect of the embodiments described above, it is possible to enable the operator to easily understand the diagnosis and treatment actions and the state of the subject which the operator wishes to check.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus comprising processing circuitry configured:
   to display a panel having a matrix formation including a plurality of sections defined by a plurality of columns and a plurality of rows, the plurality of columns respectively corresponding to a plurality of periods obtained by dividing a designated display period into sections arranged in a time series, the plurality of rows respectively corresponding to a plurality of events of diagnosis and treatment actions performed on a subject during the designated display period;
   to display, on the panel, a plurality of pieces of information respectively expressing specifics of the plurality of events performed on the subject during the display period, by displaying each of the pieces of information expressing specifics of the respective event performed during the respective period in a section defined by the corresponding column and the corresponding row included in the panel;
   to tally an index value indicating a degree of a change in the diagnosis and treatment actions or in a state of the subject, for each event and each;
   to normalize the tallied index value and then derive, based on the normalized index value, a color relatively indicating the degree of the change in the diagnosis and treatment actions or the state of the subject, for each event and each period; and
   to display, on the panel, a plurality of colors together with the plurality of pieces of information respectively expressing specifics of the plurality of events, by displaying each color derived for the respective event and the respective period in a section defined by the corresponding column and the corresponding row included in the panel.

2. The medical information processing apparatus according to claim 1, wherein
   the processing circuitry is further configured to detect that the display period is changed, and
   when detecting that the display period is changed, the processing circuitry re-tallies the index values on a basis of a display period after the change and re-derives a color on a basis of the re-tallied index values.

3. The medical information processing apparatus according to claim 1, wherein the processing circuitry arranges the color corresponding to the events to be displayed, side by side while time sequences thereof are aligned, with pieces of information indicating how many events occurred with respect to the events displayed in the time series.

4. The medical information processing apparatus according to claim 1, wherein the processing circuitry realizes a display by replacing the color corresponding to the events, with pieces of information indicating how many events occurred with respect to the events displayed in the time series.

5. The medical information processing apparatus according to claim 1, wherein the processing circuitry tallies, as the index value, values each indicating a number of critical events defined by an operator.

6. The medical information processing apparatus according to claim 1, wherein the processing circuitry tallies, as the index value, abnormality values each indicating an abnormality in the diagnosis and treatment actions or in the state of the subject.

7. The medical information processing apparatus according to claim 1, wherein the processing circuitry tallies, as the index values, how many critical events defined in advance have occurred.

8. The medical information processing apparatus according to claim 1, wherein the processing circuitry further calculates and displays pieces of information indicating differences in the index values among tally units.

9. The medical information processing apparatus according to claim 1, wherein the processing circuitry displays icons corresponding to specifics of the events in such a manner that at least one icon is arranged for each of tally units.

10. The medical information processing apparatus according to claim 9, wherein, as the icons, the processing circuitry displays icons each expressing the specifics of a corresponding one of the events by using a figure, text, or a color.

11. A medical information processing method comprising:
    displaying a panel having a matrix formation including a plurality of sections defined by a plurality of columns and a plurality of rows, the plurality of columns respectively corresponding to a plurality of periods obtained by dividing a designated display period into sections arranged in a time series, the plurality of rows respectively corresponding to a plurality of events of diagnosis and treatment actions performed on a subject during the designated display period;
    displaying, on the panel, a plurality of pieces of information respectively expressing specifics of the plurality of events performed on the subject during the display period, by displaying each of the pieces of information expressing specifics of the respective event performed during the respective period in a section defined by the corresponding column and the corresponding row included in the panel;
    tallying an index value indicating a degree of a change in the diagnosis and treatment actions or in a state of the subject, for each event and each period;
    normalizing the tallied index value and then deriving, based on the normalized index value, a color relatively indicating the degree of the change in the diagnosis and treatment actions or the state of the subject, for each event and each period; and
    displaying, on the panel, a plurality of colors together with the plurality of pieces of information respectively expressing specifics of the plurality of events, by displaying each color derived for the respective event and the respective period in a section defined by the corresponding column and the corresponding row included in the panel.

12. The medical information processing apparatus according to claim 1, wherein the plurality of colors are different colors respectively assigned to the plurality of ranges of the index values.

13. The medical information processing apparatus according to claim 1, wherein the plurality of colors are different colors respectively assigned to normalized values of the plurality of ranges of the index values.

* * * * *